(12) United States Patent
Dietzschold et al.

(10) Patent No.: US 7,223,584 B2
(45) Date of Patent: *May 29, 2007

(54) RECOMBINANT RABIES VACCINE AND METHODS OF PREPARATION AND USE

(75) Inventors: Bernhard Dietzschold, Newton Square, PA (US); D. Craig Hooper, Medford, NJ (US); Matthias J. Schnell, Harleysville, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/268,197

(22) Filed: Oct. 10, 2002

(65) Prior Publication Data

US 2003/0113346 A1     Jun. 19, 2003

Related U.S. Application Data

(60) Provisional application No. 60/328,350, filed on Oct. 10, 2001.

(51) Int. Cl.
*C12N 7/00*     (2006.01)
*C12N 7/04*     (2006.01)

(52) U.S. Cl. .................. 435/235.1; 435/236; 435/239; 424/199.1; 424/204.1; 424/211.1; 424/224.1

(58) Field of Classification Search ............. 424/184.1, 424/204.1, 199.1, 211.1, 224.1; 435/235.1, 435/236, 239
See application file for complete search history.

(56) References Cited

U.S. PATENT DOCUMENTS 5,853,735 A     12/1998 Benejean et al. ........ 424/208.1

FOREIGN PATENT DOCUMENTS

WO     WO 01/70932     9/2001

WO     WO 01/70932     * 9/2001

OTHER PUBLICATIONS

Morimoto et al. J of Neurovirology 2000, vol. 6, pp. 373-381.*
Conzelmann Annual Rev Genetics 1998, from IDS.*
Dietzschold et al. Characterization of an antigenic determinant of the glycoprotein that correlates with pathogenicity of rabies virus, PNAS 1983, vol. 80. pp. 70-74.*
Morimoto, K et al., Genetic engineering of live rabies vaccines, Vaccine, vol. 19, Issues 25-26, May 14, 2001, pp. 3543-3551.*
Dietzschold et al. New appraoches to the prevention and eradiction of rabies, Expert Rev. Vaccines 2003, vol. 2 (3). pp. 399-406.*
Chattergoon Ma et al. (2000), *Nat. Biotech*. 18: 974-979.
Conzelman K-K (1998), *Ann. Rev. Genet.* 32: 123-62.
Dietzschold B et al. (1985), *J. Virol*. 56: 12-18.
Galelli A et al. (2000), *J. NeuroVirol*. 6: 359-372.
Kothakota S et al. (1997), *Science* 278: 294-297.
Morimoto K et al. (2000), *J. NeuroVirol*. 6: 373-381.
Morimoto K et al. (1999), *J. Virol*. 73: 510-517.
Pulmanausahakul R et al. (2001), *J. Virol*. 75(22): 10800-10807.
Restifo NP (2000), *Curr. Opin. Immunol*. 12: 597-603.
Rovere P et al. (1998), *J. Immunol*. 161: 4467-4471.
Sasaki S et al. (2001), *Nat. Biotech*. 19: 543-547.
Shi Y et al. (2000), *P.N.A.S. USA* 97: 14590-14595.
Virag L. et al. (1998), *Immunol*. 94: 345-355.
Wiktor TJ (1977), *P.N.A.S. USA* 74: 334-338.
Yan X et al. (2001), *J. Neurovirol*. 7: 518-527.
Faber M et al. (2002), *Journal of Virology*, 76: 3374-3381.
Jallet C, et al. (1999), *Journal of Virology*, 73: 225-233.
Finke S, et al. (2000), *Journal of Virology*, 74: 7261-7269.
Morimoto, K et al. (2001), *Vaccine* 19, 3543-3551.

* cited by examiner

*Primary Examiner*—Bruce R. Campell
*Assistant Examiner*—Myron G. Hill
(74) *Attorney, Agent, or Firm*—Drinker Biddle & Reath LLP; Daniel A. Monaco

(57) ABSTRACT

Live rabies virus vaccines comprising a recombinant rabies virus genome which overexpresses the rabies virus G protein increase apoptotic activity in infected cells, and enhance the generation of anti-rabies immunity in a subject.

26 Claims, 8 Drawing Sheets

FIG. 1

RECOMBINANT RABIES VACCINE AND METHODS OF PREPARATION AND USE

CROSS REFERENCE TO RELATED APPLICATION

This application claims the benefit of U.S. provisional patent application Ser. No. 60/328,350, filed on Oct. 10, 2001, the disclosure of which is herein incorporated by reference in its entirety.

REFERENCE TO GOVERNMENT GRANT

The invention described herein was supported in part by Public Health Service grant no. A145097. The U.S. government has certain rights in this invention.

L. SEQUENCE LISTING

The file of this patent contains a Sequence Listing, identified as Seq. ID. Nos. 1-3. The Sequence Listing is contained in paper format (8 sheets) and in electronic format (2 CD-R 18 KB). The CD-R formats can be identified as follows:
Title: Sequence Listing for "Recombinant Rabies Vaccine and Method of Preparation and Use"
Seq. ID Nos.: 1-3
File Size: 18 KB
Date Created: Apr. 28, 2006

FIELD OF THE INVENTION

This invention relates to the field of biotechnology and immunology, and in particular to the design of recombinant live rabies virus vaccines which cause an infected cell to overexpress a rabies virus G protein.

BACKGROUND OF THE INVENTION

The rabies virus (RV) is a member of the family Rhabdoviridae. Like most members of this family, RV is a non-segmented, negative stranded RNA virus whose genome codes for five viral proteins: RNA-dependent RNA polymerase (L); a nucleoprotein (N); a phosphorylated protein (P); a matrix protein (M) located on the inner side of the viral protein envelope; and an external surface glycoprotein (G). Dietzschold B et al. (1991), Crit. Rev. Immunol. 10: 427-439.

Rabies is transmitted through broken skin by the bite or scratch of an animal infected with RV. Upon exposure, RV penetrates unmyelinated peripheral nerve endings, and travels to the nerve cell body by retrograde axonal transport. RV replicates exclusively in the neurons, and finally arrives in the CNS where it causes cellular dysfunction and death of the infected animal. Rupprecht C E et al. (1987), Lab. Invest. 57: 603. As RV spreads directly from cell to cell, it can substantially evade immune recognition. Clark H F et al. (1985), in Comparative Pathology of Viral Disease, Vol. 2, (Olson R G et al., eds.), CRC Press, Boca Raton, Fla. pg. 65.

The major immune effector against rabies is the production of virus neutralizing antibodies (VNA) elicited by RV G protein. The capacity to trigger the production of VNA depends largely on the integrity of RV G protein "spikes" on the encapsulating viral envelope, which are comprised of trimers of RV G. Dietzschold B et al. (1982), J. Virol. 44: 595-602. However, nonhumoral factors such as RV antigen-specific CD4+ T-helper cells, CD8+ cytotoxic T-cells (Cox J H et al. (1977), Infect. Immun. 16: 754-759) and innate defense mechanisms (Hooper D C et al. (1998), J. Virol. 72: 3711-3719) also play an important role in the anti-rabies immune response. As these cellular and innate immune defense mechanisms are triggered by the "internal" L, N and P proteins, optimal protective immunity against rabies is conferred by live RV vaccine.

Antiviral immunity may also be related to factors affecting the pathogenesis of RV. For example, the pathogenicity of a particular RV variant is inversely correlated with RV G expression levels, and increased G protein accumulation is positively correlated with the induction of apoptosis. Galelli A et al. (2000), J. Neuro Virol. 6: 359-372; Morimoto K et al. (1999), J. Virol. 73:510-517. Also, a stronger immune response is generated with non-pathogenic RV strains as compared to pathogenic RV strains. Wiktor T J (1977), P.NA.S. USA 74: 334-338.

Enhanced apoptosis is also known to contribute to the induction of antiviral immune responses to intracellular proteins. For example, the apoptotic death of cells after viral infection can trigger powerful innate and adaptive immune responses against the infecting virus. Restifo N P (2000), Curr. Opin. Immunol. 12: 597-603. Cell injury can also release endogenous adjuvants that stimulate cytotoxic T-cell responses. Shi Y et al. (2000), P.N.A.S. USA 97:14590-14595. Moreover, apoptotic cells can trigger the maturation and antigen-presenting function of dendritic cells, and apoptotic cells are believed to release factors that induce activation of MHC class I- and Il-restricted T cells by mature dendritic cells. Chattergoon M A et al. (2000), Nat. Biotech. 18: 974-979; Rovere P et al. (1998), J. Immunol. 161: 4467-4471. Apoptotic bodies also have the ability to deliver antigens to professional antigen-presenting cells. Sasaki S et al. (2001), Nat. Biotech. 19: 543-547.

The relationship between RV G protein expression, apoptosis and enhanced RV immunity is not clear. The quantity of RV G protein expressed on the cell surface appears to be important for triggering apoptotic pathways. Substantial sequence differences between the G proteins of highly pathogenic RV's, as compared to that of attenuated, pro-apoptotic RV's, suggests that G protein qualitative factors are also important in inducing apoptosis of infected cells.

Effective recombinant live RV vaccines have been produced by replacing the non-neurotropic G protein gene in antigenically conserved, laboratory RV strains with non-pathogenic neurotropic G genes from wild-type "street virus" strains. Such attenuated "street virus" RV vaccines retain the distinct neurotropisms of the wild-type strains, and also show higher replication efficiency and G protein expression levels than the wild-type RV. However, the "street virus" RV vaccines differ greatly in their ability to induce protective immunity. Morimoto J et al. (2000), J. Neuro Virol. 6: 373-381 and WO 01/70932.

Another live attenuated RV vaccine has been produced, in which the RV psi gene is replaced with a non-viral, pro-apoptotic gene such as cytochrome c. This vaccine causes increased apoptosis of infected primary cultured mouse neurons, and mice exposed to this vaccine show an approximately three-fold increase in VNA titers as compared to those vaccinated with control RV vaccine lacking a functional cytochrome c gene. However, these recombinant vaccines rely on expression of the non-viral pro-apoptotic gene, rather than an increase in the production of RV G protein, to enhance anti-viral immunity. See WO 01/70932, supra.

Thus, there is a need for a live, non-pathogenic RV vaccine which imparts enhanced rabies immunity to a subject without the requirement for species-specific neurotropism. Desirably, enhanced immunity should derive from increased apoptosis of infected cells due to an overexpression of RV G protein, and not from the expression of non-viral, pro-apoptotic genes.

SUMMARY OF THE INVENTION

The present invention is directed to a recombinant live RV vaccine which overexpresses an RV G protein inside an infected cell, and methods of vaccinating a subject with the recombinant live RV vaccine. Overexpression of the RV G protein from a recombinant live RV vaccine of the invention causes increased incidence of apoptosis in the infected cells, with a concomitant enhancement of the anti-rabies immune response in the subject. The recombinant live RV vaccine of the invention does not require species-specific neurotropic G proteins, and also does not contain non-viral, pro-apoptotic genes.

Thus, the invention provides a recombinant live RV vaccine comprising a recombinant RV genome which comprises at least two RV G genes.

The invention also provides a method of producing a live rabies virus vaccine, comprising the steps of inserting one or more G protein genes into a rabies virus genome which already contains a G protein gene, to produce a recombinant rabies virus genome. The recombinant rabies virus genome is then used to construct an expression vector for transfection into a host cell. The expression vector produces infectious recombinant rabies virus inside the transfected host cell, which can be recovered and used as a live vaccine against rabies.

The invention further provides a method of vaccinating a subject against rabies, comprising administering an effective amount of a live rabies vaccine of the invention, such that cells of the subject are infected with the rabies vaccine and the rabies vaccine induces overexpression of G protein in the infected cells. The overexpression of the G protein is believed to increase the apoptotic response in the infected cell, and in turn induce an anti-rabies immune response in the subject.

The invention also provides pharmaceutical compositions comprising a live recombinant rabies vaccine according to the invention, and a pharmaceutically acceptable carrier or excipient.

BRIEF DESCRIPTION OF THE DRAWINGS

Figure 1:
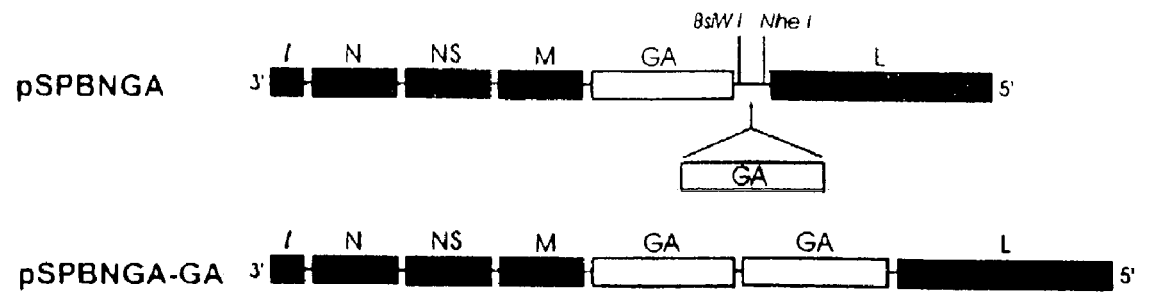

FIG. 1 is a schematic diagram of a recombinant RV genome of live RV vaccine SPBNGA-GA (SEQ ID NO: 3), which carries two copies of an RV attenuated (Arg333→Glu333) G protein gene. SPBNGA: RV genome derived from SPBN in which the original G protein gene is replaced with one copy of the attenuated G protein gene from SPBNGA-GA (SEQ ID NO: 3).

Abbreviations

Figure 2A:
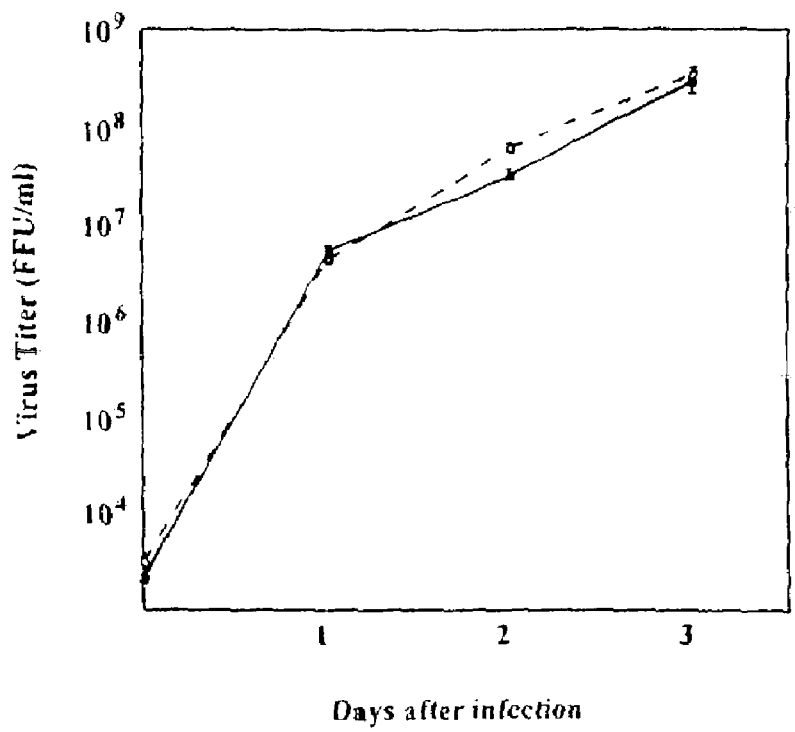
FIGS. 2A and 2B are plots showing production of recombinant and parental RV strains in BSR and NA cells, respectively. For both figures, cells were infected with SPBNGA (closed squares) and SPBNGA-GA (SEQ ID NO: 3) (open squares) at m.o.i. of 5 with incubation at 37° C. Viruses were harvested at days 1, 2 and 3 post-infection, and titrated by a fluorescent staining method. Data are given as the mean (+/−SE) of six virus titer determinations.
Figure 2B:
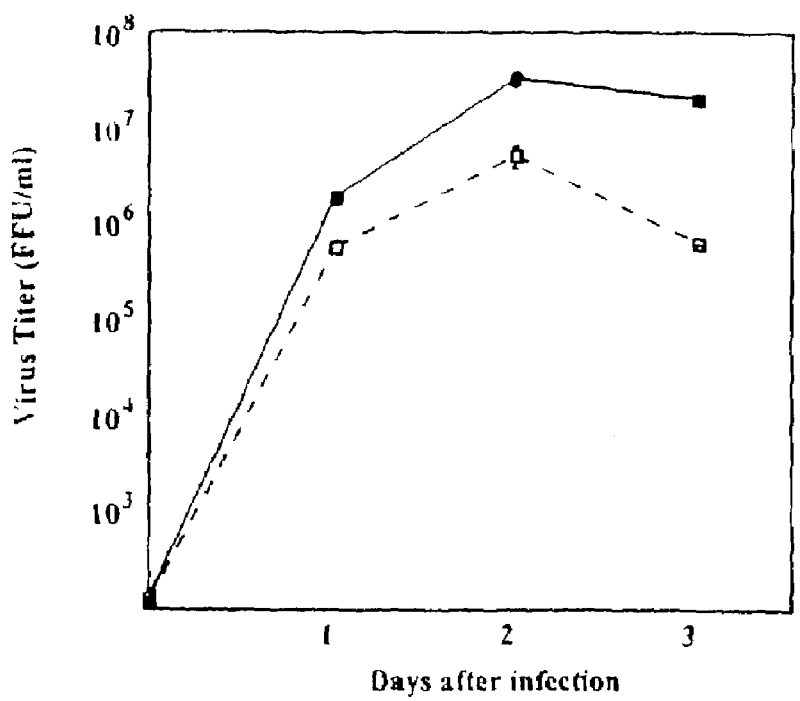
Figure 3:
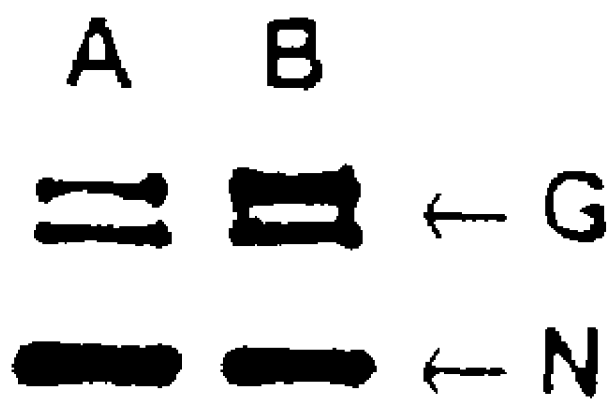
FIG. 3 is an immunoprecipitation analysis of RV G and N proteins produced from BSR cells infected with SPBNGA (lane A) or SPBNGA-GA (SEQ ID NO: 3) (lane B). Infected cells were labeled with [$^{35}$S]-methionine, lysed and immunoprecipitated with a mixture of polyclonal anti-RV G and anti-RV RNP protein antiserum. Immune complexes were separated by SDS-10% PAGE, and the gel was dried and analyzed using a storage phoshpor screen and a laser scanner.
Figure 4:
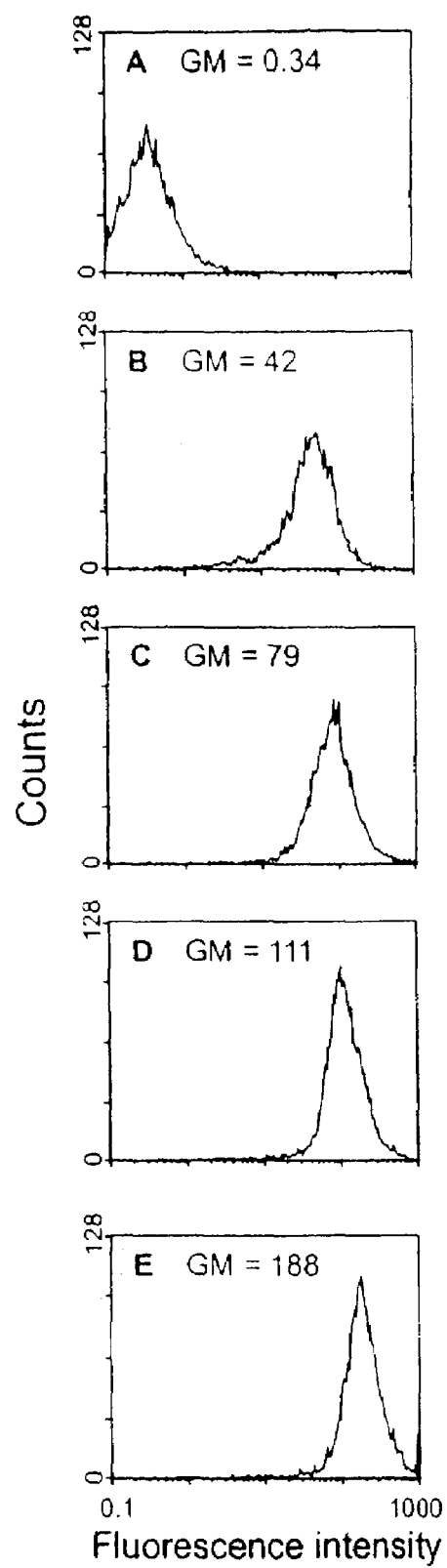
FIG. 4 is flow cytometry analysis of cell surface expression of RV G on NA cells. Cells were infected with SPBNGA (panels B, C) or SPBNGA-GA (SEQ ID NO: 3) (panels D, E). Non-infected cells were used as a control (panel A). At 24 hours (panels B, D) and 48 hours (panels C, E) post-infection, cells were incubated with a polyclonal rabbit anti-RV G antiserum, followed by FITC-conjugated anti-rabbit antibody. Surface expression was determined by flow cytometry, and fluorescence intensity was plotted. The geometric mean of the fluorescence intensity (GM) is given in each panel.
Figure 5A:
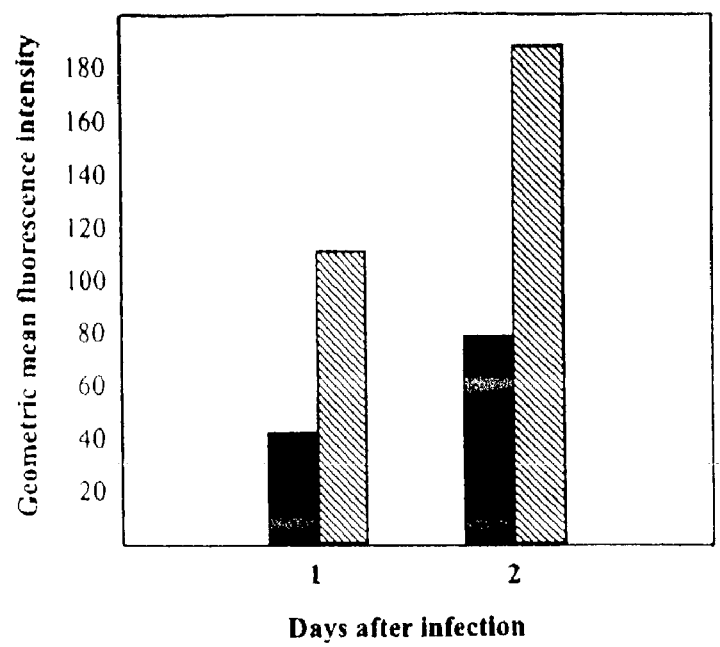
FIGS. 5A and 5B are plots comparing the effect of RV G overexpression on caspase-3 activity in NA cells infected with SPBNGA (filled bars) and SPBNGA-GA (SEQ ID NO: 3) (shaded bars) at 1 and 2 days post-infection. The geometric mean of the fluorescence of RV G on the surface of cells infected with SPBNGA (filled bars) and SPBNGA-GA (SEQ ID NO: 3) (shaded bars) from FIG. 5A was compared with caspase-3 activity measured in lysates of uninfected (crosshatched bars), SPBNGA-infected (filled bars), or SPBNGA-GA (SEQ ID NO: 3)-infected (shaded bars) NA cells from FIG. 5B. Caspase-3 activity determined in lysates of SPBNGA-GA (SEQ ID NO: 3) infected NA cells in the presence of caspase-3 inhibitor (open bars) served as a control for the specificity of the reaction.
Figure 5B:
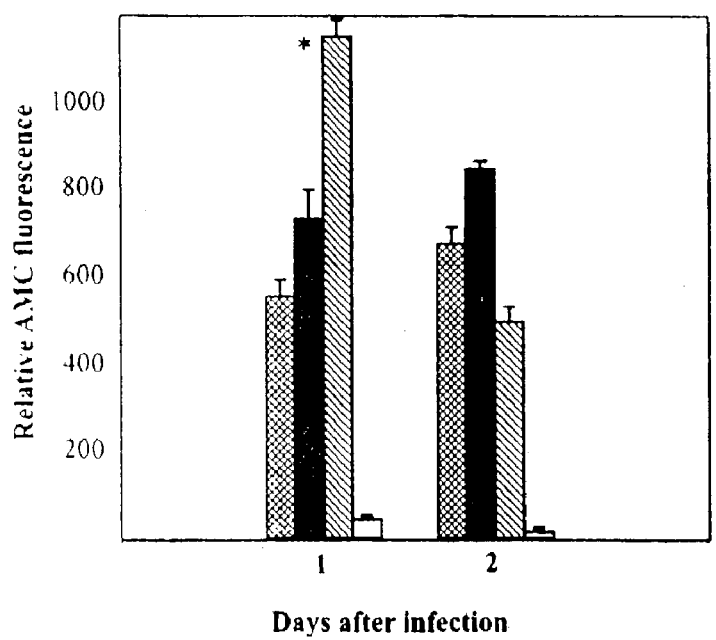
Figure 5C:
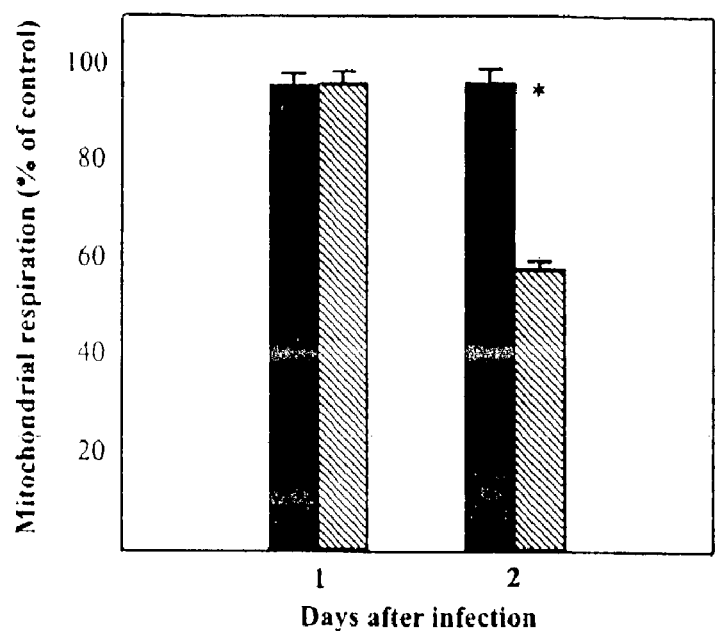
FIG. 5C is a plot comparing the mitochondrial respiration in NA cells infected with SPBNGA (filled bars) or SPBNGA-GA (SEQ ID NO: 3) (shaded bars) at 1 and 2 days post-infection. For both figures, error bars indicate standard error and asterisks indicate significant differences (p<0.01) in caspase-3 activity or mitochondrial respiration, as appropriate.

BSR cells—a cell line derived from BSK-21 cells which can be infected with RV.

CVS-N2c—a pathogenic subclone of the mouse-adapted CVS-24 rabies virus.

DTT—dithiothreitol

EDTA—ethylene diamine tetraacetic acid

ELISA—enzyme-linked immunosorbent assay

FBS—fetal bovine serum

FITC—fluorescein isothiocyanate

GMT—geometric mean titer
i.c.—intra-cranial
i.m.—intra-muscular i.p.—intra-peritoneal
i.p.—intra-peritoneal
IU—International Units
m.o.i.—multiplicity of infection
NA cells—neuroblastoma cells of A/J mouse origin
RFFIT—rapid fluorescent inhibition test
RV—rabies virus
RV-RNP—rabies virus ribonucleoprotein complex
SDS-10% PAGE—sodium dodecyl sulfate, 10% polyacrylamide gel electrophoresis
VNA—virus neutralizing antibodies
WHO—World Health Organization

DETAILED DESCRIPTION OF THE INVENTION

RV G protein is the major viral antigen responsible for the induction of VNA and protective immunity against rabies. It has now been found that live RV vaccines which comprise a recombinant RV genome engineered to overexpress RV G protein enhance the generation of anti-rabies immunity in a subject. Cells infected with the present vaccines also exhibit elevated apoptotic activity as compared to RV vaccines with unaltered G-protein expression. Without wishing to be bound by any theory, the enhanced immunogenicity of the present vaccines appears to be related to the increased apoptosis induced by the overexpression of RV G protein.

As used herein, a "subject" is a human or non-human mammal that can be infected with the rabies virus. A non-human mammal can be domesticated or feral, and includes cats, dogs, rats, mice, bats, foxes, raccoons, squirrels, opossum, coyotes, and wolves.

The present live vaccines comprise an RV genome that has been modified to overexpress the RV G protein. The modifications which produce overexpression of RV G protein can be introduced into the RV genome using recombinant DNA technology familiar to those of ordinary skill in the art.

As used herein, "RV G protein gene" or "G protein gene" means the nucleic acid sequences which, when present in an RV genome, are sufficient to encode an RV glycoprotein in an infected cell. The G protein gene thus includes a coding sequence which is flanked on the 3' end with a short transcriptional start sequence, and on the 5' end with a short transcriptional stop/polyadenylation sequence. The G gene can include an intergenic region of 1-59 untranslated nucleotides, which is located between the 5' stop/polyadenylation sequence and the 3' transcriptional start sequence of the next viral gene. See, e.g., pgs. 134-136 of Conzelman K-K (1998), Ann. Rev. Genet. 32: 123-62, the entire disclosure of which is herein incorporated by reference.

As used herein, "recombinant DNA technology" refers to the manipulation of nucleic acid molecules (including RNA) to produce a heterologous oligonucleotide sequence, using conventional molecular biology, microbiology, and recombinant techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" IIRL Press, (1986)]; B. Perbal, "A Practical Guide To Molecular Cloning" (1984), the entire disclosures of which are herein incorporated by reference.

As used herein, a "heterologous" oligonucleotide sequence comprises two or more identifiable nucleic acid sequences linked together in an arrangement which is not found in nature. Heterologous oligonucleotide sequences include naturally occurring DNA or RNA sequences which have been deliberately modified, or which have been duplicated one or more times. An allelic variation or nucleic acid sequences arising from naturally-occurring mutational events are not considered heterologous oligonucleotide sequences as defined herein.

According to the present invention, RV G protein overexpression is induced by increasing the G protein gene copy number in the RV genome. RV genomes typically have one copy of the G protein gene. Thus, one or more additional G protein genes can be inserted into the RV genome to produce an recombinant RV genome capable of expressing higher amounts of G protein, as compared to RV genomes having only one G protein gene. As transcription from the RV genome initiates at the single polymerase entry site at the 3' tenninus and is obligatorily processive, it is expected that G protein expression from a recombinant RV genome of the invention would increase proportionally with the number of G protein genes present in the genome. For example, an RV genome comprising two G protein genes would have approximately twice the G protein expression than the corresponding RV genome with only one G protein gene; recombinant RV genomes with three protein genes would have approximately three times the G protein expression, etc. Thus, as used herein, "overexpression of a G protein gene" refers to the increased expression of the G protein from the recombinant RV genome of the invention, which increase in G protein expression is proportional to the number of additional G protein genes in the recombinant RV genome.

The additional copies of the RV G protein gene can be inserted into the RV genome adjacent to the existing G protein gene, or can be inserted into other areas of the RV genome that do not significantly interfere with viral transcription and replication. The additional G protein genes can also be inserted in place of RV genomic sequences such as the psi gene. Preferably, the additional G protein genes are inserted into the RV genome adjacent to the existing G protein gene.

The additional copies of the RV G protein gene can derive from any RV strain, but preferably comprise a neurotropic G protein gene sequence from a wild-type or "Street virus." For example, the G protein genes from the highly neurotropic RV strains CVS-N2c, CVS-B2c, DRV-4, RRV-27, SRV-16 and SHBRV-18 can be used. These RV strains are well-known in the art; see, e.g., WO 01/70932; Morimoto K et al. (1999), .J. Virol. 73: 510-517; Monmoto K et al. (1996), P.N.A.S. USA 93: 5653-5658; and Monmoto K et al. (2000), J. Neuro Virol. 6: 373-381, the entire disclosures of which are herein incorporated by reference. The additional copies of the G protein gene can also be derived from attenuated laboratory RV strains such as SAD B19, SPBN, SN-10, and SN 10-333 (see, e.g., Schnell M J et al (1994), EMBO J. 13: 4195-4203 and Morimoto K et al. (2001) and Schnell M J et al. (2000), P.N.A.S. USA 97: 3544-3549, the entire disclosures of which are herein incorporated by reference), or from "fixed" strains such as PM, LEP, SAD and ERA, which are also well-known in the art (see, e.g., Smith J S et al. (1995), Sem. in Virol 6: 387-400, the entire disclosure of which is herein incorporated by reference). The additional copies of the RV G protein gene inserted into the RV genome can be the same or different than the existing G protein gene, but are preferably identical.

Preferably, both the existing G protein gene and the G protein to be inserted into the RV genome are modified to produce a recombinant RV genome which is attenuated. As used herein, "attenuated" or "attenuation" is defined as either a genetic mechanism involving premature termination of transcription from the RV genome, or immunologically as a process whereby a pathogenic RV loses its virulence. Many methods for modifying G protein sequences to produce viral attenuation known. For example, the pathogenicity of a particular rabies virus is related to a G protein determinant that interacts with putative cell surface receptors (Coulon P et al. (1982), J. Gen. Virol. 61: 97; Coulon P et al. (1983), .J. Gen. Virol. 64: 693-696; and Dietzschold B et al. (1983), P.N.A.S. USA 80:70-74, the entire disclosures of which are herein incorporated by reference). Alteration of this G protein determinant can attenuate pathogenicity of the RV. In particular, substitution of arginine at position 333 of the G protein for glutamine or glycine results in a slowdown of virus uptake and a complete loss of pathogenicity of certain RV strains (e.g., ERA, CVS-11). See Dietzschold B et al. (1983), P.N.A.S. USA 80:70-74, supra and Dietzschold B et al. (1985), J. Virol. 56:12-18, the entire disclosure of which is herein incorporated by reference.

Deletions or other alterations within the G protein cytoplasmic domain, such that the cytoplasmic tail of the G protein no longer binds to the RNP-M complex, will also attenuate the pathogenicity of an RV strain. For example, replacing the cytoplasmic domain of a particular G protein with that from another RV strain will render the RV apathogenic when administered i.m. See Morimoto K et al. (2000), J. Neuro Virol. 6:373-381, supra.

Recombinant RV genomes according to the invention can comprise any number of additional G protein genes which do not significantly interfere with RV transcription or replication. For example, one, two, three, four or more additional G protein genes can be added to an RV genome to produce the recombinant RV genomes of the invention. In a preferred embodiment, the recombinant RV genome comprises one additional G protein gene.

As stated above, standard recombinant DNA technology can be used to obtain additional G protein genes, optionally modify them to effect viral attenuation, and insert them into an RV genome. For example, recombinant RV genomes of the invention can be constructed by first obtaining (by cloning, restriction digestion and isolation, or otherwise) one or more G protein gene sequences for insertion into an RV genome. Site directed mutagenesis, restriction and re-ligation with heterologous sequences, or some other appropriate technique can optionally be performed to modify the G protein sequences such that the vaccine ultimately produced is attenuated. The RV genome is then digested with the appropriate restriction enzymes and the additional G protein sequences are inserted. The proper insertion of the additional G genes can be confirmed using techniques such as restriction enzyme analysis and/or DNA sequencing.

The present vaccine comprises a live, infectious RV particle comprising a recombinant RV genome as described above. Live, infectious viral particles for use as the vaccine of the invention can be recovered or "rescued" by transfecting appropriate host cells with an expression vector containing a recombinant RV genome into which additional G protein genes have been inserted. Insertion of the recombinant genome into an expression vector for subsequent transfection into host cells for production of vaccine is within the skill in the art.

As used herein, an "expression vector" is a genetic element that functions as an autonomous unit of DNA replication under its own control sequence, to which another DNA segment may be attached or inserted so as to bring about replication of the attached or inserted segment. Expression vectors include plasmids, phages or cosmids. In general, expression vectors contain promoter sequences which facilitate the efficient transcription and translation of the attached or inserted DNA segment in a particular host cell. The expression vector also typically contains an origin of replication and transcription terminator(s), as well as specific genes which are capable of providing phenotypic selection in transfected host cells.

As used herein, a "promoter sequence" is a regulatory region capable of binding RNA polymerase in a cell and initiating transcription of a downstream (3') coding sequence. For purposes of definition, the promoter sequence is bounded at its 3' terminus by the transcription initiation site and extends upstream (5' direction) to include the minimum number of bases or elements necessary to initiate transcription at levels detectable above background. One of ordinary skill in the art can select an appropriate promoter for use in an expression vector for a particular host cell. Suitable promoters for use in the present invention include the T7 promoter.

As used herein, a "transfected" cell is one into which an exogenous or heterologous nucleic acid sequence has been introduced. The nucleic acid sequence which has been introduced can be integrated into the genome of the transfected cell, or can be maintained episomally. A stably transfected cell is one in which the introduced DNA has integrated into a chromosome so that it is inherited by daughter cells through chromosome replication.

The expression vector containing the modified RV genome should comprise a promoter, such as a T7 promoter, which is active in the host cell. For example, BSR cells stably transfected with a T7 polymerase gene, as described in Buchholz U J et al. (1999), J. Virol. 73: 251-259, the entire disclosure of which is herein incorporated by reference, can be used as a host cell. These cells constitutively express T7 polymerase, which can activate transcription from a T7 promoter contained with the expression vector. At an appropriate time after transfection (e.g., three days), infectious recombinant RV vaccine can be recovered from the culture media of the transfected host cells. Infectivity of the recovered live vaccine can be confirmed by exposing BSR cells to culture media from the transfected host cells, or to the recovered live vaccine. Rescued live vaccine can be visualized in these BSR cells by staining the cell culture with FITC-labeled anti-RV protein antibodies.

Construction and rescue of an exemplary attenuated live RV vaccine of the invention called SPBNGA-GA (SEQ ID NO: 3), which comprises an RV genome containing two identical G protein genes, is set forth in the Examples below.

Rescued live vaccine according to the invention can be used to vaccinate a subject against rabies. In the present method, a subject can be vaccinated against rabies by delivery of an effective amount of the present live vaccine by any enteral or parenteral route of administration. A preferred enteral route of administration is oral; e.g., through food-baits designed to vaccinate wild animal populations. Suitable parenteral routes of administration include i.m., i.p., i.c., subcutaneous, or exposure to the vaccine through a break or scratch in the skin.

As used herein, an "effective amount" of the live vaccine refers to an amount of the vaccine which, when administered, produces an anti-rabies immune response in a host. The production of an anti-rabies immune response in a subject vaccinated with a vaccine of the invention can be confirmed using techniques known in the art; for example, by measuring antibody titers to RV protein antigens, or by determining the vaccinated subject's ability to survive subsequent challenge with a pathogenic RV. Exemplary techniques to measure an anti-rabies immune response in a vaccinated subject are given below in the Examples; see the techniques entitled "VNA Assay," "ELISA Assay of Anti-RV G and Anti-RV RNP Antibody Titers," "Immunization and Virus Challenge;" and Example 5.

Cells of a subject that are infected with the present live vaccine overexpress the RV G protein. The amount of G protein expression in cells infected with a vaccine of the invention can be measured by well-known techniques such as Western blot analysis, Northern blot analysis or quantitative RT-PCR, and immunoprecipitation.

The overexpression of the G protein in cells infected with the present live vaccines is related to an increase in the apoptotic response of these cells. Without wishing to be bound by any particular theory, it appears that the increased apoptotic response causes an enhanced anti-rabies immune response in the subject. The presence of an enhanced anti-rabies immune response can be confirmed by comparing the anti-RV protein antibody titers in a subject vaccinated with a conventional live RV vaccine, to those of a subject vaccinated with vaccines of the invention (see, e.g., Example 5 below).

The live vaccines of the invention can be formulated into pharmaceutical compositions according to techniques known in the art, for example as described in Remington's Pharmaceutical Science, 17th ed., Mack Publishing Company, Easton, Pa. (1985), the entire disclosure of which is herein incorporated by reference. Pharmaceutical compositions of the present invention are characterized as being at least sterile and pyrogen-free. As used herein, "pharmaceutical formulations" include formulations for human and veterinary use. The present pharmaceutical formulations may comprise at least one live vaccine of the invention mixed with a physiologically acceptable carrier medium to form solutions, suspensions or dispersions. Suitable physiologically acceptable carrier media include water, buffered water, saline, buffered saline, dextrose, glycerol, ethanol or combinations thereof.

Pharmaceutical compositions comprising vaccines of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA, CaNaDTPA-bisamide), or, optionally, additions (e.g., 1 to 50 mole percent) of calcium or sodium salts (for example, calcium chloride, calcium ascorbate, calcium gluconate or calcium lactate). Pharmaceutical compositions of the invention can be packaged for use in liquid form, or can be lyophilized. For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

The preparation of food-baits containing vaccines of the invention is also within the skill in the art. For example, the preparation of food-baits containing live RV vaccines is disclosed in Wandeler Al et al. (1988), Rev. Infect. Dis. 10 (suppl. 4): 649-653 and Aubert M F A et al., pp. 219-243, in Lyssaviruses (Rupprecht C E et al., eds.), Springer-Verlag, New York, 1994; and Fu Z F et al., pp. 607-617, in New Generation Vaccines ($2^{nd}$ Edit.) (Levine M M et al, eds.), Marcel Dekker, Inc., New York, 1997, the entire disclosures of which are herein incorporated by reference.

The invention will now be illustrated by the following non-limiting examples.

Materials and Methods Used in Examples

Viruses. Viral Antigens, and Cells

CVS-N2c is a subclone of the mouse-adapted CVS-24 RV, as described in Morimoto K et al. (1998), P.N.A.S. USA 95: 3512-3156, the entire disclosure of which is herein incorporated by reference.

The RV SN-10 was generated from a SAD B19 cDNA clone as described in Schnell M J et al (1994), EMBO .J 13: 4195-4203, supra, and Morimoto K et al. (2001), Vaccine 19: 3543-3551, the entire disclosures of which are herein incorporated by reference.

RV G and RV RNP were isolated from purified SNIO virus or SN1O-infected cells as described in Dietzschold B on pp. 175-179 of Lyssaviruses (Rupprecht C E et al, eds.), Springer Verlag, New York, 1996, the entire disclosure of which is herein incorporated by reference.

Neuroblastoma NA cells of A/J mouse origin were grown at 37° C. in RPMI 1640 medium supplemented with 10% fetal bovine serum ("FBS").

BSR cells, a cloned cell line derived from BHK-21 cells, were grown at 37° C. in Dulbecco's modified Eagle's medium supplemented with 10% FBS.

Primary neuron cultures were prepared from the hippocampi of prenatal Swiss Webster mice as described Morimoto K Ct al. (1999), 0.1. Virol. 73: 510-517, supra.

Virus Infectivity Assay

Infectivity assays were performed at 34° C. or 37° C. on monolayers of NA or BSR cells in 96-well plates as described in Wiktor T J (1977), P.N.A.S. USA 24: 334-338, the entire disclosure of which is herein incorporated by reference. All titrations were carried out in triplicate.

Immunoprecipitation Analysis

BSR cells grown in T 25 tissue culture flasks were infected with the live RV vaccines SPBNGA or SPBNGA-GA (SEQ ID NO: 3) (see below) at a m.o.i. of 5 and incubated 24 h later with [$^{35}$S] methionine (100 microCi/ml) for 2 h at 37° C. A mixture of polyclonal antisera against RV N and G proteins (as described in Pulmanausahakul R et al. (2001), .J Virol in press) was used for immunoprecipitation. The labeled immunocomplexes were adsorbed to protein A-Sepharose beads (Protein A Sepharose™ Fast Flow, Amersham Pharmacia Biotech, Piscataway, N.J.) and analyzed by SDS-10% PAGE. The gel was dried and analyzed using a storage phosphor screen and a Molecular Imager FX Pro Plus (Bio-Rad, Hercules, Calif.) with QuantityOne software (Bio-Rad, Hercules, Calif.).

Flow Cytometry

NA cells were infected with the live recombinant RV vaccines at a m.o.i. of 1 and incubated for 24 or 48 h at 34° C. Cells were suspended in PBS containing 50 mM EDTA, pelleted at 130×g for 5 mm, resuspended in 50 microliters of PBS, and fixed in suspension by addition of 500 microliters of 4% paraformaldehyde solution. After 20 mm, cells were washed twice with PBS containing 10 mM glycine and 1% BSA (PBS-glycine-BSA), and incubated with rabbit anti-rabies G antiserum (1:400) followed by FITC-conjugated affinity-purified goat anti-rabbit antibody (1:200, Jackson Immuno Research Laboratories Inc., West Grove, Pa.). Flow cytometry was performed on an EPICS profile analyzer.

Mitochondrial Respiration Assay

The mitochondria-dependent reduction of MTT (3-[4,5-dimethylthiazol-2yl]2,5-diphenyltetrazolium bromide; Sigma, St. Louis, Mo.) was used as an indicator of mitochondrial respiration, as described in Virag L et al. (1998), Immunol. 24: 345-355, the entire disclosure of which is herein incorporated by reference. At 24 and 48 h postinfection, NA cells were incubated with 0.2 mg/ml MTT for 1 h at 37° C. and lysed with DMSO. The extent of reduction of MTT to formazan was quantitated by measurement of $OD_{550}$ using a microplate reader.

Caspase-3 Activity Assay

Caspase-3 activity was measured as the cleavage of the fluorogenic tetrapeptideamino-4-methylcoumarmne conjugate (DEVD-AMC) using a caspase-3 assay kit (BD Pharmingen, San Diego, Calif.). At 24 and 48 h postinfection, $10^6$ RV vaccine-infected NA cells were trypsinized, washed with icecold PBS and lysed with lysis buffer (10 mM HEPES, 2 mM EDTA, 0.1% CHAPS, 1 mM PMSF, 10 microgram/ml pepstatin A, 10 microgram/ml aprotinin, 2 microgram/ml leupeptin, pH 7.2). After centrifugation at 14,000 rpm, 200 microliter of supernatant was added to 200 microliter of reaction buffer (200 mM HEPES, 20% sucrose, 0.1% CHAPS, 5 microliter/ml 1 M DTT, pH 7.25) supplemented with 2 microliter/rnl caspase-3 substrate or caspase-3 inhibitor. The reaction mixture was incubated for 1 h at 37° C. and fluorescence was measured with a fluorimeter using 400 nm excitation and 505 nm emission wavelength.

Fluorescence Staining and Confocal Microscopy

Primary neuron cultures were infected with the SPBNGA and SPBNGAGA (see below) at a m.o.i. of 5 and incubated at 37° C. To detect DNA strand breaks indicative of apoptotic cell death, the infected neurons were fixed with 4% paraformaldehyde at 24 and 48 h post-infection and subjected to the terminal deoxynucleotidyltransferase-mediated dUTP nick end-labeling (TUNEL) assay as described Morirnoto et al. (1999), J. Virol. 73: 510-517, supra. For immunofluorescence analysis, infected neurons were fixed with 4% paraformaldehyde at 24 and 48 h post-infection, permeablized by incubation with 0.1% Triton X-100 and stained with FITC-labeled anti rabies N protein monoclonal antibody (Centocor, Malvem, Pa.), as described Morirnoto et al. (1999), supra. To visualize neurofilarnents, the infected neurons were fixed and permeablized as above and incubated with monoclonal antibodies anti MAP2 clone AP-20 (Sigma, St. Louis, Mo.) and FITC-labeled polyclonal rabbit anti-mouse IgG antibodies (Jackson ImmunoLaboratories, West Grove, Pa.). Polymerized and non-polymerized actin (F and G) were detected with rhodamine-conjugated phalloidin and Oregon Green 488 deoxyribonuclease I (Molecular Probes, Eugene, Oreg.), respectively, according to the manufacturer's recommendations. Fluorescent-labeled cells were analyzed by confocal microscopy, and images were processed using Confocal Assistant (Version 4.02) software.

Immunization and Virus Challenge

Groups of ten 8 to 10 week-old female Swiss Webster mice (Taconic Farms, Germantown, N.Y.) were inoculated i.m. with 100 microliters of serial 10-fold dilutions of live recombinant RV vaccines. After 10 days, blood was collected from each mouse and the animals were injected i.c. under isofluorane anesthesia with 10 microliters containing 100 $LD_{50}$ of CVS-N2c. Mice were observed for 4 weeks for clinical signs of rabies. Mice that showed definitive clinical signs of rabies such as paralysis, tremors, and spasms were euthanized by $CO_2$ intoxication.

Survivorship rates obtained with the different vaccine dilutions were compared between the different vaccination groups and the 50% effective dose (EDSO) was calculated as described in Wilbur L A et al. (1996) in Ch. 37, pp. 360-368 of Laboratory Techniques in Rabies (Meslin F-X et al, eds.), WHO, Geneva, the disclosure of which is herein incorporated by reference.

VNA Assay

Mice were bled from the retro-orbital sinus under isofluorane inhalation anesthesia, and about 100 microliters of blood was collected from each mouse. Mouse sera were tested for the presence of VNA using the rapid fluorescent inhibition test (RFFIT) as described Wiktor T J (1977), supra. Neutralization titers, defined as the inverse of the highest serum dilution that neutralizes 50% of the challenge virus, were normalized to IU using the WHO anti-rabies virus antibody standard. Geometric mean titers (GMT) were calculated from individual titers of 10 mice that received identical concentrations of the same vaccine virus.

ELISA Assay of Anti-RV G and Anti-RV RNP Antibody Titers

RV G and RV N-specific antibodies present in mice after vaccination with the recombinant live RV vaccines were assessed in direct ELISA using RV G or RV RNP at a concentration of 1 microgram/ml as trapping antigens. Antigen-coated MaxiSorp™ surface plates (Nunc, Denmark) were incubated with serial dilutions of antibody obtained from SPBNGA- and SPBNGA-GA (SEQ ID NO: 3) immunized mice and the amount of bound antibody was determined using horseradish peroxidase-conjugated anti-mouse IgG (ICN Biomedicals, Inc. Costa Mesa, Calif.). O-phenylendiaminedihydrochloride (Sigma, St. Louis, Mo.) was used for color development of peroxidase-conjugated antibodies, and the activity was read at 400 nm. Data were analyzed using DeltaSoft ELISA software (Bio Metallics, Inc., Princeton, N.J.).

EXAMPLE 1—CONSTRUCTION OF HIGHLY ATTENUATED LIVE RV VACCINES HAVING ONE OR TWO IDENTICAL COPIES OF RV G PROTEIN GENE

To further reduce pathogenicity of the RV vaccine vector SPBN described in McGettigan J P et al (2001), 1 Virol. 75: 8724-8732, the entire disclosure of which is herein incorporated by reference, the coding region of SPBN 0 was replaced with a similar RV G gene containing the single amino acid exchange Arg333→Glu333 (AGA→GAG). For this approach, RV G was amplified by PCR using Vent polymerase (New England Biolabs, Beverly, Mass.) from SN10-333 as described in Morimoto K et al. (2001), Vaccine 19: 3543-3551, supra, and cloned into SPBN. The resulting plasmid was designated pSPBN-GA. To construct a recombinant RV genome expressing two identical RV G proteins, the G gene to be inserted was amplified by PCR using Vent polymerase, using SN10-333 as the template with the primers SN-10 BsiWI (sense) CGATGTATACGTACGAAGAT-GTTCCTCAGCTCTCCTG (SEQ ID NO: 1) [BsiWI site underlined, start codon in boldface] and SN-10 NheI (antisense) CTTATCAGCTAGCTAGCTAGTTA-CAGTCTGTCTCACCCCCA (SEQ ID NO: 2) [NheI site underlined, stop codon in boldface]. The PCR product was digested with BsiWI and NheI (New England Biolabs, Beverly, Mass.) and ligated to pSPBNGA, which had been digested previously with BsiWI and NheI. The resulting plasmid was designated pSPBNGA-GA (SEQ ID NO: 3) (see FIG. 1 for schematic of recombinant genome). The sequences of both GA genes in pSPBNGA-GA (SEQ ID NO: 3) were confirmed by restriction analysis and DNA sequencing.

Recombinant live viruses were rescued as described in Schnell M J Ct al (1994), EMBO J. 13: 4195-4203, supra, and Morimoto K et al. (2001), Vaccine 19: 3543-3551, supra; and Schnell Mi et al. (2000), P.N.A.S. USA 97: 3544-3549, supra. Briefly, BSR-T7 cells were transfected using a calcium phosphate transfection kit (Stratagene, La Jolla, Calif.) with 5.0 micrograms of pSPBNGA or pSPBNGA-GA (SEQ ID NO: 3) and 5.0 micrograms of pTIT-N, 2.5 micrograms of pTIT-P, 2.5 micrograms of pTIT-L, and 2.0 micrograms of pTIT-G. After a 3-day incubation, supernatants were transferred onto BSR cells and incubation continued for 3 days at 37° C. Cells were examined for the presence of rescued virus by immunostaining with FITC-labeled anti-rabies virus N protein antibody (Centocor, Malvern, Pa.). The correct nucleotide sequences of the inserted genes were confirmed by RT-PCR and DNA sequencing.

EXAMPLE 2—GROWTH OF RECOMBINANT RV AND RV G PROTEIN EXPRESSION IN VITRO

Comparison of the time course of recombinant virus production in BSR cells infected with SPBNGA or SPBNGA-GA (SEQ ID NO: 3) (FIG. 2A) revealed no differences, indicating that the insertion of an additional GA gene did not affect virus replication. In NA cells, however, fewer infectious SPBNGA-GA (SEQ ID NO: 3) particles than SPBNGA particles were produced (FIG. 2B). The lower virus titers produced in SPBNGA-GA (SEQ ID NO: 3)-infected as compared to SPBNGA-infected NA cells are most likely due to an higher potential of the former cells to undergo apoptosis.

Immunoprecipitation analysis of RV G expressed in infected BSR cells indicated markedly higher expression levels in SPBNGA-GA (SEQ ID NO: 3) infected cells than in SPBNGA-infected cells (FIG. 3). The G:N ratio was 0.22 in SPBNGA infected cells and 0.50 in SPBNGA-GA (SEQ ID NO: 3)-infected cells; i.e., approximately a 2-fold higher G expression level due to the additional G gene. The relative cell surface expression of G on NA cells at 24 and 48 h post-infection as measured by flow cytometry revealed 1.9 times higher and 1.7 times higher cell surface expression levels, respectively, in SPBNGA-GA (SEQ ID NO: 3) infected than in SPBNGA infected cells (FIG. 4, compare panels D and E with B and C). Thus, an increase in RV G production is reflected in higher accumulation of G on the cell surface.

EXAMPLE 3—EFFECT OF G PROTEIN OVEREXPRESSION ON CELL VIABILITY

To analyze the effects of overexpressed G protein on cell viability, the cell surface expression levels of G (FIG. 5A) were compared with caspase-3 activity (FIG. 5B) and mitochondrial respiration (FIG. 5C) in infected NA cells at 1 and 2 days post-infection. Caspase-3 activity, as determined by the formation of the fluorogenic tetrapeptide amino-4-methylcoumarine (AMC), was increased by 32% in SPBNGA-infected cells as compared to uninfected cells at 1 day post-infection, with no significant change at 2 days post-infection in SPBNGA infected cells. By contrast, caspase-3 activity increased by 87% ($p<0.01$) in SPBNGA-GA (SEQ ID NO: 3) infected cells at 1 day post-infection, but markedly decreased by 35% as compared with uninfected cells at 2 days post-infection. Whereas no significant differences between SPBNGA and SPBNGA-GA- (SEQ ID NO: 3) infected NA cells in mitochondrial respiration were detected at 1 day post-infection, SPBNGAGA-infected cells showed a 40% decrease ($p<0.01$) in mitochondrial respiration at 2 days post-infection, while SPBNGA-infected NA cells remained unchanged.

Comparison of the values obtained from the caspase-3 and the mitochondrial assays with the expression levels of G protein strongly suggests an association between the level of G protein cell surface expression and the extent of cell injury. The decrease in mitochondrial respiration seen in SPBNGA-GA (SEQ ID NO: 3) infected NA cells was prevented by addition of caspase-3 inhibitors to the culture medium, indicating that the cytotoxic effect observed in these cells is primarily due to activation of the apoptosis cascade from overexpression of the RV G protein.

EXAMPLE 4—EFFECT OF RV G OVEREXPRESSION ON THE MORPHOLOGY OF CULTURED PRIMARY NEURONAL CELLS

Immunofluorescence analysis in combination with confocal microscopy of N protein expression in SPBNGA-GA (SEQ ID NO: 3)-infected primary hippocampal neuron cultures revealed large N protein-positive inclusion bodies in the cell body cytoplasm, and only limited N protein-specific staining in neuronal processes at 24 h post-infection. In contrast, SPBNGA-infected neurons showed a finer granular N-protein staining pattern, which extended into the neuronal processes. Although almost no N protein staining of neuronal processes could be visualized in either SPBNGA- or SPBNGA-GA (SEQ ID NO: 3)-infected neurons at 48 h post-infection, the degeneration of cell bodies was much more pronounced in SPBNGA-GA (SEQ ID NO: 3) infected neurons. No substantial changes in neurofilament staining were detected in SPBNGA-infected neurons at 24 h post-infection as compared to uninfected neurons; however, neurofilament staining was already markedly reduced at this time in SPBNGA-GA (SEQ ID NO: 3) infected neurons, particularly in the neuronal processes. Double immunofluorescence analysis of F and G actin in uninfected and infected neurons revealed a strong reduction of F actin staining in SPBNGA-GA (SEQ ID NO: 3)-infected neurons at 48 h post-infection, which was not seen in SPBNGA-infected neurons. TUNEL staining visualized a large number of positive nuclei in SPBNGA-GA (SEQ ID NO: 3) infected neurons at 24 and 48 h post-infection, whereas only a few stained nuclei were detected in SPBNGA-infected neurons at the same time points.

The decrease in F actin staining after infection with SPBNGA-GA (SEQ ID NO: 3) is consistent with apoptosis-induced depolymerization of the actin filaments (see Kothakota S T et al. (1997), Science 278: 294-297). Furthermore, the number of TUNEL-positive nuclei was greatly increased in SPBNGA-GA (SEQ ID NO: 3)-infected neurons as compared with uninfected and SPBNGA-infected neurons, indicating that overexpressed RV G leads to activation of the apoptosis cascade. Without wishing to be bound by any particular theory, it is possible that RV G expression induced by the live viral vaccines of the invention that exceeds a certain threshold severely perturbs the cell membrane, resulting in the activation of signaling proteins that trigger apoptosis.

EXAMPLE 5—EFFECT OF RV G OVEREXPRESSION ON IMMUNITY

Figure 6A:
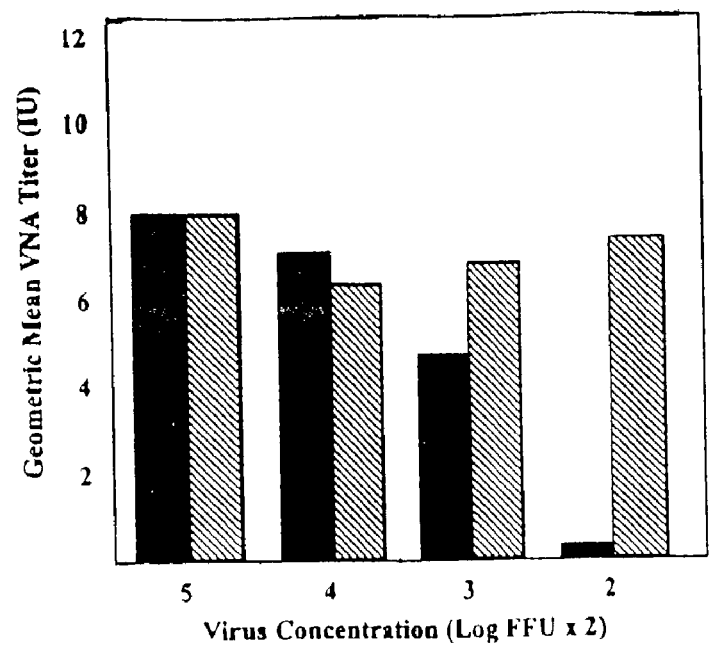
FIG. 6A is a plot of VNA titers of groups of 10 mice injected with serial 10-fold dilutions of SPBNGA (filled bars) or SPBNGA-GA (SEQ ID NO: 3) (shaded bars), as determined with the RFFIT test. VNA titers were normalized to IU using the WHO standard, and are given as geometric mean titers.

Analysis of the VNA responses in mice inoculated i.m. with serial dilutions of SPBNGA or SPBNGA-GA (SEQ ID NO: 3) indicated no major differences in geometric mean VNA titers (expressed as GMTs) of mice that received $10^5$ and $10^4$ FFU of the live viral vaccines (FIG. 6A). However, while the VNA GMTs of mice immunized with $10^3$ and $10^2$ FFU of SPBNGA strongly decreased in a dose-dependent manner, the VNA GMTs of mice immunized with the same concentrations of SPBNGA-GA (SEQ ID NO: 3) remained essentially unchanged. The VNA GMT of mice immunized with 102 FFU of SPBNGA-GA (SEQ ID NO: 3) was 24 times higher than that of mice immunized with the same amount of SPBNGA.

Figure 6B:
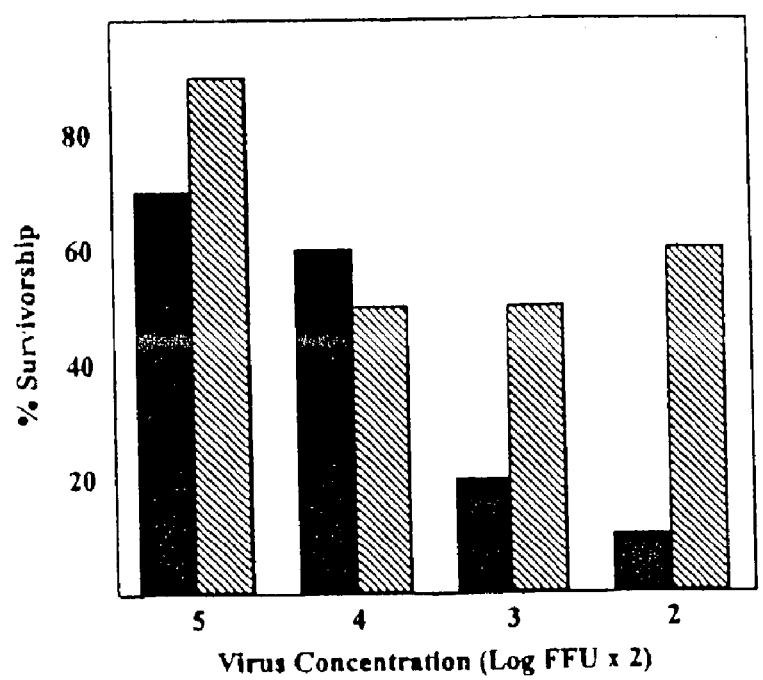
FIG. 6B is a survivorship plot of mice immunized SPBNGA (filled bars) or SPBNGA-GA (SEQ ID NO: 3) (shaded bars), which were challenged i.c. with 100 LD50 of CVS-N2c two weeks after immunization. Survivorship was determined at 4 weeks post-challenge.
Figure 6C:
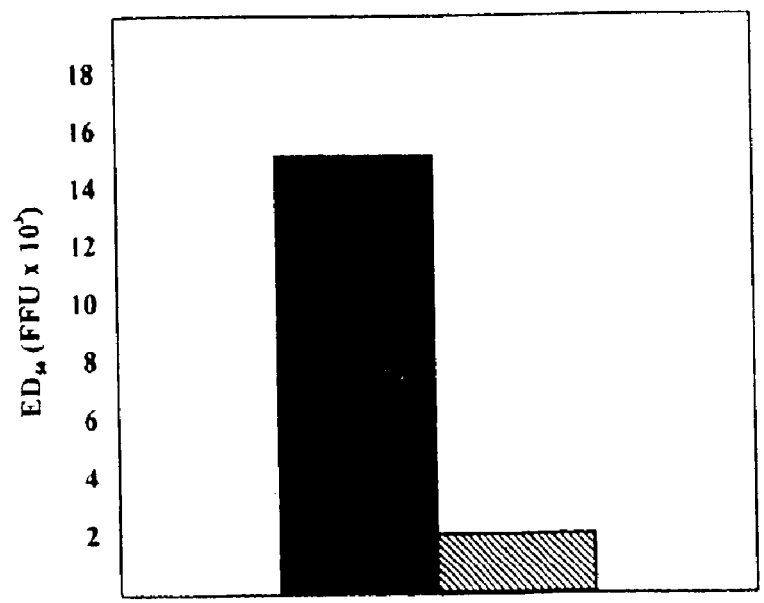
FIG. 6C shows the ED50 values for the SPBNGA (filled bars) or SPBNGA-GA (SEQ ID NO: 3) (shaded bars) vaccination groups.

These data are paralleled by the results of a virus challenge experiment which demonstrated that survivorship in mice vaccinated i.m. with 10 and 10 FFU of SPBNGA-GA (SEQ ID NO: 3), which are subsequently challenged i.c. with 100 $LD_{50}$ of CVS-N2c virus, was markedly higher than that of mice immunized with SPBNGA (FIG. 6B). The $ED_{50}$ calculated from the mortality rates in the different vaccine dilution groups (FIG. 6C) indicated an 8-fold higher efficacy of SPBNGA-GA (SEQ ID NO: 3) as compared with SPBNGA, demonstrating that overexpression of RV G strongly enhances the protective immunity against rabies.

ELISA analysis of antibodies directed against RV G and RV RNP showed that mean anti-G and anti-N antibody titers Thus, mice immunized i.m. with $10^3$ and $10^2$ FFU SPBNGA-UA developed markedly higher VNA titers than mice immunized with the same concentration of SPBNGA. The higher VNA titers in SPBNGA-GA (SEQ ID NO: 3)-immunized mice conferred greater protection against a lethal i.c. challenge infection with the highly pathogenic rabies virus strain CVS-N2c. Survivorship was markedly higher in mice immunized with SPBNGA-GA (SEQ ID NO: 3) as compared to mice that received SPBNGA, with $ED^{50}$ values 8 times lower in the SPBNGA-GA (SEQ ID NO: 3) group.

The ELISA assays of the sera obtained from SPBNGA- and SPBNGAGA-immunized mice revealed similar profiles for the anti-N and anti-G antibody titers induced by the two viruses. Since the major phenotypic difference between SPBNGA- and SPBNGA-GA (SEQ ID NO: 3)-infected cells is the greater induction of apoptosis in the latter, it seems likely that, again without wishing to be bound by any theory, the elevated apoptotic activity of SPBNGA-GA (SEQ ID NO: 3) accounts for its increased immunogenicity.

All documents referred to herein are incorporated by reference in their entirety. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

---

SEQUENCE LISTING

<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Primer

<400> SEQUENCE: 1
cgatgtatac gtacgaagat gttcctcagc tctcctg        37

<210> SEQ ID NO 2
<211> LENGTH: 41
<212> TYPE: DNA
<213> ORGANISM: Artificial Sequence
<220> FEATURE:
<223> OTHER INFORMATION: Primer

<400> SEQUENCE: 2
cttatcagct agctagctag ttacagtctg tctcaccccc a       41

Figure 7A:
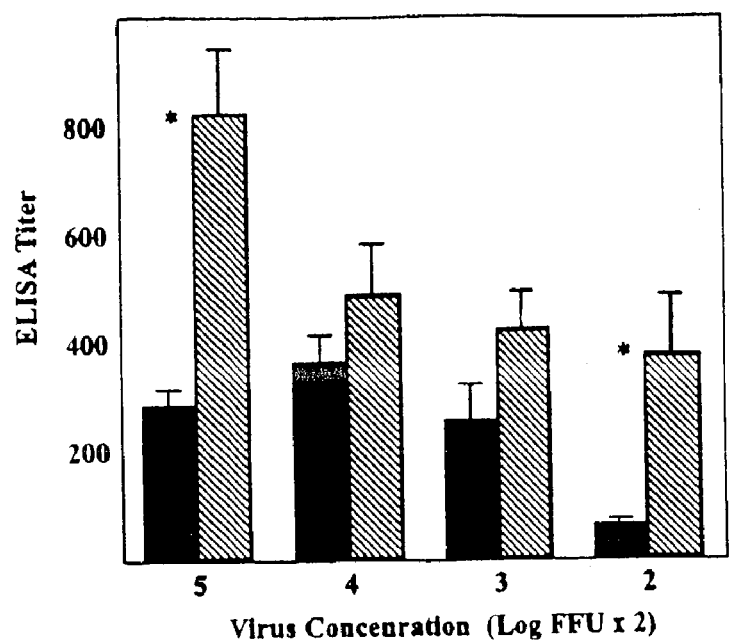
FIGS. 7A and 7B are plots comparing the titers of antibodies specific for RV G or RV RNP, respectively, in mice immunized with different concentrations of SPBNGA (filled bars) or SPBNGA-GA (SEQ ID NO: 3) (shaded bars). Antibody titers were determined by direct ELISA using RV G or RV RNP as the trapping antigens. Error bars indicate standard error, and asterisks indicate statistically significant differences (p<0.01) between antibody titers induced by SPBNGA or SPBNGA-GA (SEQ ID NO: 3).
Figure 7B:
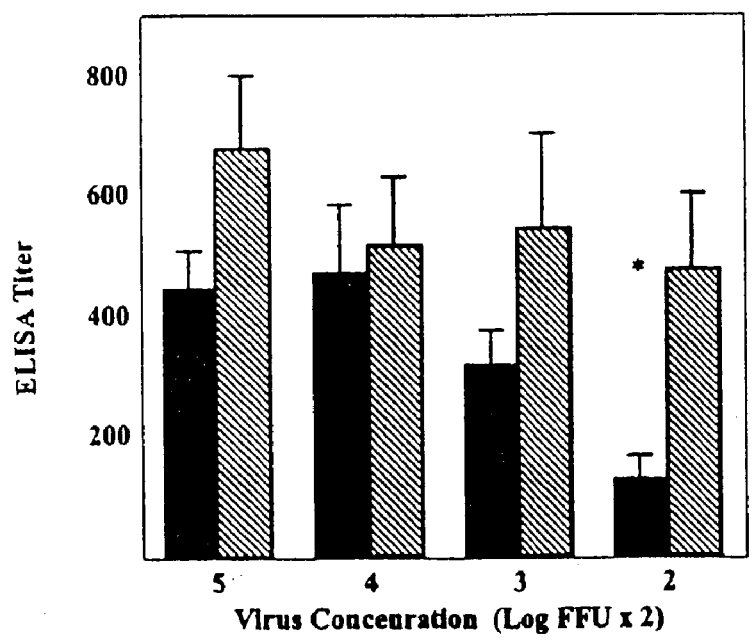

--- were higher in SPBNGA-GA (SEQ ID NO: 3) than in SPBNGA-immunized mice, regardless of the dose of virus used for immunization (FIGS. 7A and 7B). As was the case for VNA GMTs, maximal differences in anti-G and anti-N antibody titers were seen in the mice that received the lowest amount of vaccine, indicating that overexpression of RV G enhances the immune response not only against the homologous RV G, but also against viral antigens such as the RV RNP.

We claim:

1. A live attenuated rabies vaccine comprising a recombinant rabies virus genome, wherein the recombinant rabies genome comprises at least two rabies G protein genes.

2. The rabies vaccine of claim 1, wherein the rabies virus genome comprises two G protein genes.

3. The rabies vaccine of claim 1, wherein the at least two G protein genes are identical.

4. The rabies vaccine of claim 1, wherein at least one of the at least two G protein genes are from said attenuated rabies virus strains selected from the group consisting of; ERA; SAD B19; SPBN; SN-10; SN10-333; LEP; and SAD.

5. The rabies vaccine of claim 1, wherein the recombinant rabies genome is SPBNGA-GA (SEQ ID NO: 3).

6. A method of producing a live rabies virus vaccine, comprising the steps of: (1) inserting one or more G protein genes into a rabies virus genome which already contains a G protein gene, to produce a recombinant rabies virus genome; (2) constructing an expression vector from the recombinant rabies virus genome; (3) transfecting a cell with the expression vector and recovering infectious recombinant rabies virus for use as a live rabies virus vaccine.

7. The method of claim 6, wherein the recombinant rabies virus genome comprises two G protein genes.

8. The method of claim 6, wherein the G protein genes are identical.

9. The method of claim 6, wherein at least one of the G protein genes derive from rabies virus strains selected from the group consisting of; ERA; SAD B19; SPBN; SN-10; SN10-333; LEP; and SAD.

10. The method of claim 6, wherein the recombinant rabies genome is SPBNGA-GA (SEQ ID NO: 3).

11. A method of vaccinating a subject against rabies, comprising administering an effective amount of the live attenuated rabies vaccine according to claim 1 to the subject, such that cells of the subject are infected with the live attenuated rabies vaccine and the live attenuated rabies vaccine induces overexpression of G protein in the infected cells, wherein an anti-rabies immune response is produced in the subject.

12. The method of claim 11, wherein the subject is a human.

13. The method of claim 11, wherein the subject is a non-human animal.

14. The method of claim 13, wherein the non-human animal is selected from the group consisting of cats; dogs; rats; mice; bats; foxes; raccoons; squirrels; opossum; coyotes; and wolves.

15. The method of claim 11, wherein the rabies vaccines is administered enterally.

16. The method of claim 15, wherein the enteral administration comprises oral administration.

17. The method of claim 16, wherein the oral administration comprises administration through food-baits designed to vaccinate wild animal populations.

18. The method of claim 11, wherein the live attenuated rabies vaccine is administered parenterally.

19. The method of claim 18, wherein the parenteral administration is selected from the group consisting of intramuscular; intra-peritoneal; intra-cranial; subcutaneous; or through a break in the skin.

20. The method of claim 11, wherein the recombinant rabies virus genome comprises two G protein genes.

21. The method of claim 11, wherein the G protein genes are identical.

22. The method of claim 11, wherein at least one of the at least two G protein genes are from attenuated rabies virus strains selected from the group consisting of; ERA; SAD B19; SPBN; SN-10; SN10-333; PM; LEP; and SAD.

23. The method of claim 11, wherein the recombinant rabies genome is SPBNGA-GA.

24. A pharmaceutical composition comprising the live rabies vaccine of claim 1 and a pharmaceutically acceptable carrier or excipient.

25. The pharmaceutical composition of claim 24, wherein the recombinant rabies genome comprises two G protein genes.

26. The pharmaceutical composition of claim 24, wherein the recombinant rabies virus genome is SPBNGA-GA (SEQ ID NO: 3).

* * * * *